United States Patent [19]

Wagner

[11] Patent Number: 4,656,129

[45] Date of Patent: Apr. 7, 1987

[54] ASSAY FOR A LIGAND BY USE OF SUPPORTED BINDER AND SAC LYSING AGENT

[75] Inventor: Daniel B. Wagner, Raleigh, N.C.

[73] Assignee: Becton Dickinson and Company, Franklin Lakes, N.J.

[21] Appl. No.: 641,462

[22] Filed: Aug. 16, 1984

[51] Int. Cl.$^4$ .................. G01N 33/53; G01N 33/566; G01N 33/543
[52] U.S. Cl. ........................................ 435/7; 435/810; 436/501; 436/518; 436/829
[58] Field of Search ............... 436/503, 504, 829, 819, 436/519, 520, 532, 527, 545, 546, 518, 539, 540, 821, 501; 435/7, 810

[56] References Cited

U.S. PATENT DOCUMENTS

| 3,646,346 | 2/1972 | Catt | 436/531 X |
| 3,850,578 | 11/1974 | McConnell | 23/230 |
| 4,342,739 | 8/1982 | Kakimi et al. | 436/823 X |
| 4,517,303 | 5/1985 | Freytas et al. | 436/301 |

FOREIGN PATENT DOCUMENTS

| 2041517 | 9/1980 | United Kingdom | 436/829 |
| 2069133 | 8/1981 | United Kingdom | 436/829 |

*Primary Examiner*—Sidney Marantz
*Assistant Examiner*—Jack Spiegel
*Attorney, Agent, or Firm*—Elliot M. Olstein

[57] ABSTRACT

In a homogeneous assay, binder supported on a solid support, having a sac lysing agent conjugated thereto, is contacted with analyte and tracer comprised of sacs containing a detectable marker. The sacs of the bound tracer portion are lysed to release marker to determine analyte in the sample.

20 Claims, No Drawings

ASSAY FOR A LIGAND BY USE OF SUPPORTED BINDER AND SAC LYSING AGENT

This invention relates to an assay for a ligand (analyte) and products used in such assay. More particularly, this invention relates to an assay for an analyte in which the sensitivity of the assay is increased, as well as products used in such assay.

Immunoassay methods, in general, are based on the competition between a specific analyte, the amount of which is to be determined in a sample, and a known amount of the analyte or appropriate analog thereof in labeled form (tracer) for a limited number of available binding sites on a binder which is specific towards the analyte and tracer. Thus, in a system containing an unknown amount of analyte, a known amount of tracer and a limited known amount of binder, the greater the concentration of analyte in the sample, the less the tracer will be bound by the binder.

If the concentration of tracer and binder is fixed and the only variable is the level of analyte, it is possible to establish an assay system for measuring the unknown level of analyte by determining the amount of bound and free tracer in the system. Commonly labels include radioisotopes, fluorescent dyes, enzymes, chemiluminescent materials, and the like. The activity of the radioisotope, the fluorescent intensity of the dye or the activity of the enzyme on a substrate is compared with the values given by a range of known amounts of the analyte treated in the same manner. The values obtained from the determination of the standard samples are used for establishing a standard calibration curve for the specific system and this curve is then used to determine an unknown concentration of the analyte in a known sample.

In such assays, sensitivity is of prime importance, in that in many cases, it is necessary to measure low analyte levels.

In an attempt to provide more sensitive assays, tracers have been produced for use in the assay wherein the tracer is comprised of the analyte to be assayed or appropriate analog thereof coupled to a sac which includes a detectable marker therein. In such an assay, the amount of marker which can be included in the sac is greater than the amount of marker which can be directly linked to the analyte or appropriate analog thereof, whereby each mole of tracer has in excess of one mole of marker, which increases the sensitivity of the assay. It would be desirable to employ such an assay in a manner which would not require separation of bound and free tracer portions produced in the assay (homogeneous assay).

In accordance with one aspect of the present invention, there is provided an assay wherein a sample containing a ligand to be determined (an analyte) is contacted with a binder for at least the analyte in the presence of a tracer comprised of a ligand coupled to sacs containing a detectable marker. The ligand of the tracer is bound by one of the analyte and binder. The amount of tracer which is bound to the binder is dependent upon the amount of analyte in the sample (the analyte and tracer compete for binding sites on the binder or the tracer is bound to the binder through the analyte). The assay is effected in a manner such that tracer, which is bound to the binder (directly or indirectly) comes into contact with a sac lysing agent. As a result of such contact the lysing agent lyses the sacs of the bound tracer, thereby releasing marker. Since the amount of bound tracer available for lysing by the lysing agent is dependent upon the amount of analyte present in the sample, the amount of marker which is released from the sacs and/or the rate at which the marker is released, is indicative of the amount of analyte in the sample.

In accordance with a preferred aspect of the present invention, the assay is effected as a solid phase assay with the binder and sac lysing agent both being supported on an appropriate solid support. In such an assay, the sacs of the bound tracer remain in contact with the supported lysing agent to effect lysing of the sacs, and the sacs of the free portion of the tracer do not remain in contact with the sac lysing agent for a sufficient period of time to permit effective lysing of the sacs.

Thus, in accordance with this aspect of the present invention, the bound portion of the tracer is subjected to lysing action by the lysing agent to release detectable marker, and the amount of the bound portion of the tracer is inversely proportional to the amount of analyte in the sample.

In accordance with the present invention, the assay may be a homogeneous assay in that the amount and/or rate of release of detectable marker is dependent upon the amount of bound tracer whereby the assay may be accomplished without separating the bound and free portions.

In accordance with a preferred aspect of the invention, the lysing agent may be conjugated to the supported binder, i.e., the lysing agent is supported on the solid support by being conjugated (coupled) to the supported binder. It is to be understood, however, that in some cases, it may be possible to separately support the lysing agent and binder on the solid support and still provide a homogeneous assay in which the rate and/or amount of marker released is dependent on the amount of bound tracer.

The sacs, which include a marker in the interior thereof, which are employed in the assay may be any one of a wide variety of sacs, which can be lysed by a sac lysing agent. Such sacs are generally known in the art, and vesicles, including liposomes or lipid vesicles (single walled, or multi-lamellar), polymer microcapsules (for example, those made by coascervation, or interfacial polymerization), etc. As should be apparent, the sac employed in the assay is coordinated with the sac lysing agent attached to the ligand forming the conjugate, so that the sac is lysed or ruptured upon contact with the sac lysing agent.

Polymer microcapsules are produced by procedures known in the art, except that the solution in which the microcapsules are formed also includes a marker whereby the interior of the polymer microcapsule includes the marker. The preparation of such microcapsules is disclosed for example in *Microencapsulation Processes and Applications*, edited by Jan E. Vandegger (Plenum Press 1974).

As known in the art, liposomes can be prepared from a wide variety of lipids, including phospholipids, glycolipids, steriods, relatively long change alkyl esters; e.g., alkyl phosphates, fatty acid esters, e.g. lecithin, fatty amines and the like. A mixture of fatty materials may be employed such as a combination of neutral steroid, a charged amphiphile and a phospolipid. As illustrative examples of phospholipids there may be mentioned sphingomyelin, dipalmitoyl, lecithin, and the like. As representative steriods, there may be mentioned cholesterol, cholestanol, lanosterol, and the like. As representative examples of charged amphiphilic compounds, which generally contain from 12 to 30 carbon atoms, there may be mentioned mono- or dialkyl phosphate ester, quaternary ammonium salts, or an alkylamine; e.g., dicetyl phosphate, distearyl amine, dihexadecyl amine, dilauryl phosphate, dioctadecyl sulfonate, didodecyl dioctylammonium formide, and the like.

The liposome sacs may be prepared in an aqueous solution including the marker, whereby the sacs will include the marker in the interior thereof. The liposome sacs are easily prepared by vigorous agitation in the solution, followed by removal of the marker from the exterior of the sac other procedures are also available.

Further details with respect to the preparation of sacs are set forth in U.S. Pat. No. 4,342,826 and PCT International Publication No. W080/01515, as well. "Liposomes: From Physical Structure to Therapeutic Applications," C. G. Knight, Ed. Elsevier, 1981, and "Membrane Mimetic Chemistry" by Janos H. Fendler. John Wiley and Sons, 1982 all of which are hereby incorporated by reference.

The sac lysing agent may be any one of a wide variety of materials which is capable of lysing the sac employed in the assay, with the particular sac lysing agent employed being dependent upon the sacs employed in the assay. The preferred lysing agent is an enzyme, and the enzymes capable of lysing different sacs would be known to those skilled in the art. Thus, for example, phospholipases are suitable enzymatic lysing agents. A protease enzyme is known to be effective for lysing a gelatine microcapsule.

The marker which is included within the sac may be any of a wide variety of detectable markers, including but not limited to, radioisotopes, enzymes (in the use of an enzyme, the marker and lysing agent should be different enzymes), a chromogen (an absorbing dye or a fluorescent material), a luminescent compound, spin labels, etc. Such detectable markers, and the methods for determining the markers are generally known in the art, and no further details in this respect are deemed necessary for a complete understanding of the invention. Representative examples of preferred types of markers are:

a. Dyes with a high extinction coefficient, such as sulforhodamine B and copper phthalocyanine tetrasulfonic acid, and oxazine 4 perchlorate.

b. Fluoroscent dyes, such as carboxyflurescein, organic chelates of europium and terbium, various coumarins and rhodamines.

c. Enzymes other than the lysing enzymes, such as horseradish peroxidase, which can be determined, after lysis, by a colorimetric, fluorescent, luminescent, or electrochemical (amperometric) device.

As hereinabove indicated, the tracer which is employed in the assay is a ligand having sacs coupled thereto with the sacs including a detectable marker in the interior thereof. The ligand which is employed in producing the tracer is dependent upon the assay which is employed. Thus, for example, if the assay is for an analyte which is an antigen or a hapten, the ligand portion of the tracer may be the analyte or appropriate analog thereof or in some cases may be an antibody for the analyte.

As used herein, the term "appropriate analog", when referring to an analog of the analyte, means that the analog of the analyte is bound by the binder for the analyte which is used in the assay. If the analyte is an antibody, the ligand portion of the tracer maybe an antigen bound by the antibody or an antibody elicited in response to the analyte or the antibody.

The ligand portion of the tracer is bound by one of the binder or the analyte. Thus, for example, in a so called "sandwich" assay, the analyte may be bound by the binder and the tracer bound by the analyte, whereby the amount of tracer bound to the binder through the analyte is dependent on the amount of analyte in the sample.

The above types of assays and others should be apparent to those skilled in the art from the teachings herein.

The ligand portion of the tracer may be coupled to the sacs by procedures which are generally known in the art for coupling one compound to another. Thus, for example, the sacs may be coupled to the ligand portion of the tracer by covalent coupling, derivitization, activation, and the like.

The sacs may be coupled to the ligand portion of the tracer by the use of an appropriate coupling or spacer compound (one that does not destroy the immunoreactivity of the ligand). As known in the art, the coupling compound has two reactive functional groups, one of which functional groups is capable of reacting or being linked to a functional group of the ligand portion of the tracer, and the other of which is capable of reacting or being linked to a functional group on the sacs. For example, the spacer or coupling compound, which includes at least two reactive substituent groups, may contain either a carboxyl, isocyanate, isothiocyanate, amino, thiol, hydroxy, sulfonyl, carbonyl, etc., substituent group, which, as should be apparent, is dependent upon the functional group present in the ligand and sacs which are to be coupled to each other.

Alternatively, the sacs may be coupled directly to the ligand. Thus, for example, if the ligand portion of the tracer has an amino substituent group, and the sac portion of the tracer has a carbonyl or carboxyl substituent group, then the ligand and sacs may be directly conjugated to each other by procedures known in the art; for example, an active ester technique.

The binder which is used in the assay is one which is specific for the analyte. In the case where the analyte is an antigen or a hapten, the binder may be an antibody or a naturally occurring binder which is specific for the analyte. In the case where the analyte is an antibody, then the binder employed in the assay may be either an antigen or an antibody elicited in response to the antibody to be assayed, whereby the binder is specific for the analyte.

As hereinabove indicated, in accordance with one aspect of the present invention, the binder and sac lysing agent are supported on a solid support, and in a particularly preferred embodiment, the sac lysing agent is coupled to the supported binder. The solid supports which may be employed are any one of a wide variety of solid supports which are capable of supporting the binder. As representative examples of suitable supports, there may be mentioned various polymers such as polypropylene, polystyrene, polyacrylamide, etc.; glass beads; celluose; bacterial cells; etc. Solid supports are generally known in the art, and as a result, no further disclosure in this respect is deemed necessary for a complete understanding of the present invention.

The binder may be supported on the solid support by procedures generally known in the art. In some cases, depending on the support, the binder may be adsorbed onto the support. In other cases, it may be necessary to employ covalant coupling for supporting the binder on the support.

The solid support may take a wide variety of forms. Thus, for example, the support may be in sheet form, in the form of a tube, in the form of particles, etc. Such various forms are known in the art, and no further details in this respect are deemed necessary for a complete understanding of the invention.

The assay of the present invention may be employed for determining a wide variety of analytes, and has particular applicability of those analytes which are generally found in low concentrations in the material to be assayed. As representative examples of such analytes, there may be mentioned:

Cardiac glycosides, such as digoxin and digitoxin. Antiasthmatics, such as theophyllin. Antibiotics, such as gentamicin and tobramycin. Antineoplastics, such as methotrexate. Anticonvulsants, such as phenobarbital, carbamezapine and valparic acid. Antiarrythmics, such as lidocaine and quinidine. Hormones, such as T4, T3, hCG, TSH, and various steriods. The invention is not limited to the representative examples.

In accordance with one aspect of the assay of the present invention, a sample containing or suspected of containing the analyte is incubated with a tracer, which is the analyte or appropriate analog thereof coupled to sacs including a detectable marker, a binder (specific for both the analyte and tracer) and a sac lysing agent, with the binder and lysing agent both being supported on a solid support. The incubation results in competition between the tracer and analyte for binding sites on the binder, with the amount of tracer which is bound to the binder being inversely proportional to the amount of analyte in the sample.

The incubation is effected under conditions which prevent premature rupturing of the sacs (the sacs are only ruptured by contact with lysing agent which is exterior to the sacs). This portion of the assay is generally run in an appropriately buffered aqueous medium which is isotonic with the osmolarity of the sacs. Thus, conditions of temperature, pH and ionic concentration are controlled to prevent premature rupturing of the sacs. Thus, for example, an aqueous buffered medium is provided which is isotonic with the osmolarity of the sacs. In general, the buffer provides a pH in the order of from 5 to 9.

As a result of the contact between the bound tracer and the lysing agent the sacs of the bound tracer are ruptured to release marker. The rate at which marker is released into the medium is dependent upon the amount of tracer, with an increasing amount of bound tracer resulting in an increase in the rate of release of marker into the medium. Thus, by determining the rate at which marker is released into the medium, or in the alternative, by determining the amount of marker in the medium after a fixed period of time, and comparing such values with those obtained by an identical procedure using known amounts of analytes (standard analytes having known concentration), there can be obtained a measurement of the amount of analyte present in the sample.

The rate can be determined either kinetically by measuring the signal intensity increase with time, or by the end-point method, where the reaction is allowed to proceed for a fixed length of time, and it is then stopped (for example, by increasing the pH), and the color (or fluorescence, or luminescence, as the case may be) is measured. The higher the reaction rate, the stronger will be the signal at the endpoint.

The sample volum which is used in the assay is selected so as to prevent a "run-away" rate for release of the marker, i.e., to provide a detectable rate of change with time. Thus, as the expected analyte concentration increases, the sample volume is decreased so as to provide for a detectable change in rate.

In a preferred embodiment, the binder having sac lysing agent coupled thereto may be supported on a solid support such as the walls of a tube, and in such a case, the bound and free portions of the tracer need not be separated from each other in that unbound tracer fraction does not contact the supported lysing agent for a time which is sufficient to effect significant lysing whereby the rate and/or amount of marker released is dependent on the bound tracer.

In accordance with a further aspect of the invention, there is provided a reagent kit or package for accomplishing an assay for an analyte, which includes: (a) a tracer comprised of the analyte to be assayed or appropriate analog thereof conjugated to sacs including detectable marker in the interior thereof (preferably liposomes); and (b) a solid support having supported thereon a binder for the analyte and a sac lysing agent for the sacs of the tracer. In accordance with a particularly preferred aspect, the sac lysing agent is coupled to the supported binder. The components of the kit may be included in the kit or package in separate containers; for example, vials; however, in some cases one or more of the components may be combined into a single vial. The kit may also include other components such as standards of the analyte (analyte samples having known concentrations of the analyte), known buffers, and the like.

The assay may be used to determine analyte in body fluids, such as serum, urine, etc.

The invention will be further described with respect to the following examples; however, the scope of the invention is not to be limited thereby:

EXAMPLE I

Preparation of Distearoylphosphatidylethanolamine-Digoxigenin

Distearoylphosphatidylethanolamine (400.0 mg, 0.5346 mmol, Avanti Polar Lipid) was suspended in 50 ml of $CHCl_3:CH_3OH(9:1)$ and heated to reflux under a nitrogen atmosphere until all solid had dissolved. The solution was allowed to cool followed by the addition of 3-ketodigoxigenin (207.7 mg, 0.5346 mmol) and 2.0 g of 4A sieves (Sigma). The reaction mixture was allowed to stir at 60° C. for 3 hr under a nitrogen atmosphere at which time sodium cyanoborohydride (36.95 mg, 0.5831 mmol, Sigma) was added. The mixture was then allowed to stir at room temperature overnight. The reaction was filtered and concentrated under reduced pressure to yield a white foam (579.6 mg) that appeared as one major spot and several minor spots upon TLC analysis (silica 20%, $CH_3OH:CH_2Cl_2$). The spot was visualized by Phosphomolybdic Acid Spray Reagent (Sigma), $R_f 0.3$.

The crude product was purified by low pressure column chromatography (silica gel, 10% $CH_3OH-CH_2Cl_2$) to yield the product as a white solid (185.3 mg). The product was detected by a variable wavelength UV detector set at 239 mm.

EXAMPLE II

Preparation of a Tracer: Digoxin-Labeled With a Dye-Loaded Liposome

To a 100 ml flask, add cholesterol (48 mg) distearoylphosphatidylcholine (104 mg), distearoylphosphatidylethanolamine-digoxigenin (0.5 mg), and a mixture of diisopropyl ether (6.0 ml) and methanol (1.0 ml). Evaporate the solution on a rotary evaporator, and remove the last trace of organic solvent by high vaccum evaporation. Add a solution of carboxyfluorescein (0.1M) in Tris buffer (50 mM, containing 100 mM NaCl, ph 8.0. Swirl to disperse the lipids, and then sonicate for 8 minutes at room temperature. The nonencapsulated marker can be removed by ultracentrifugation ($3 \times 75,000$ g for 30 minutes).

EXAMPLE III

Solid-Supported Anti-Digoxin-Phospholipase Conjugate

Phospholipase is conjugate to anti=digoxin antibody by a standard method (see: Kia-Ki Han, Claude Richard and Andre Delacourte, *Int. J. Biochem.* 16, (2) 129-145, 1984). A solution of this conjugate (1.0 mg/ml) in Tris buffer (pH 9.2) is incubated in polystyrene test tubes for 18 hours at 4° C. The tubes are decanted and washed with a solution of 1% BSA in the same buffer.

EXAMPLE IV

Assay Procedure

A. To anti-digoxin-phospholipase-coated tubes add:
1. Digoxin standard or serum sample (50 ul).
2. Tracer: the concentration of the tracer depends on the immunological activity of the digoxin on the surface of the dye-loaded lipsomes. This should be optimized for each tracer preparation. The tracer should be suspended in phosphate buffer, pH 7.4.
3. Incubate at room temperature at 30 minutes.
4. Read fluorescence (excitation at 488, fluorescence at 520 nm).
5. For sample, compare to standard curve produced from standards.

The present invention is particularly advantageous in that it is possible to effect a homogeneous assay for an analyte; i.e., the bound and free tracer portions need not be separated (isolated) from each other. In addition, amplification high signal to analyte ratios is achieved in the homogeneous assay.

Numerous variations and modifications of the present invention are possible in light of the above teachings and, therefore, within the scope of the appended claims, the invention may be practiced otherwise than as particularly described.

What is claimed is:

1. An assay for an analyte in a sample, comprising:
 contacting a solid support with both tracer and analyte in a sample, said solid support prior to the contacting having supported thereon both a sac lysing agent and a binder for at least the analyte, said tracer comprising a ligand coupled to sacs having a detectable marker, said contacting producing a bound tracer phase and a free tracer phase, said bound tracer phase coming into contact with supported sac lysing agent to release detectable marker by lysing of sacs of bound tracer; and determining marker released from the sacs as a measure of analyte.

2. The assay of claim 1 wherein the sac lysing agent and the binder are separately supported on the solid support.

3. The assay of claim 1 wherein the sac lysing agent is conjugated to the binder which is supported on the solid support.

4. The assay of claim 1 wherein the detectable marker is a chromogen.

5. The assay of claim 4 wherein the sac is a liposome.

6. The assay of claim 4 wherein the binder is an antibody.

7. The assay of claim 1 wherein the ligand portion of the tracer is bound by the binder for the analyte.

8. The assay of claim 1 wherein the lysing agent is an enzyme.

9. The assay of claim 1 wherein the marker released from the sacs is determined without separating the bound tracer portion from the sample.

10. The assay of claim 9 wherein the sample is serum.

11. The assay of claim 10 wherein the solid support is a tube.

12. The assay of claim 11 wherein the sac is a liposome containing a chromogen as a detectable marker and the lysing agent is an enzyme.

13. A reagent kit for use in an assay for analyte in a sample wherein the solid support is contacted with both tracer and analyte with the solid support prior to the contacting having supported thereon both the sac lysing agent and a binder for at least the analyte, comprising:
 a package, said package including a solid support having supported thereon a binder for at least the analyte and a sac lysing agent; and a tracer comprising a ligand coupled to sacs having a detectable marker, said sacs being capable of being lysed by said sac lysing agent.

14. The kit of claim 13 wherein the sac lysing agent and the binder are separately supported on the solid support.

15. The kit of claim 13 wherein the sac lysing agent is conjugated to the binder which is supported on the solid support.

16. The kit of claim 13 wherein the detectable marker is a chromogen.

17. The kit of claim 16 wherein the sac is a liposome.

18. The kit of claim 16 wherein the lysing agent is an enzyme.

19. The kit of claim 13 wherein the solid support is a tube.

20. The kit of claim 13 wherein the sac is a liposome and the lysing agent is an enzyme.

* * * * *